United States Patent [19]

Yamazaki et al.

[11] Patent Number: 4,910,275
[45] Date of Patent: Mar. 20, 1990

[54] DENTAL MATERIAL

[75] Inventors: Noboru Yamazaki, Tokyo; Shigeaki Kurata, Kokubunji; Toshiharu Yagi, Takarazuka; Hiroshi Inukai, Settsu, all of Japan

[73] Assignee: Daikin Industries, Ltd., Osaka, Japan

[21] Appl. No.: 237,427

[22] Filed: Aug. 29, 1988

[30] Foreign Application Priority Data

Aug. 28, 1987 [JP] Japan .................................. 62-215936

[51] Int. Cl.$^4$ ............................................. C08F 18/20
[52] U.S. Cl. .................................... 526/246; 526/245; 526/323.1
[58] Field of Search ....................... 526/245, 246, 323.1

[56] References Cited

U.S. PATENT DOCUMENTS 4,616,073 10/1986 Antonucci ............................ 526/245
4,725,631 2/1988 Bastioli et al. ....................... 526/246

Primary Examiner—Joseph L. Schofer
Assistant Examiner—Alex H. Walker

[57] ABSTRACT

A dental material comprising a copolymer which comprises at least 10% by weight of a polymeric unit of at least one of the following monomers:

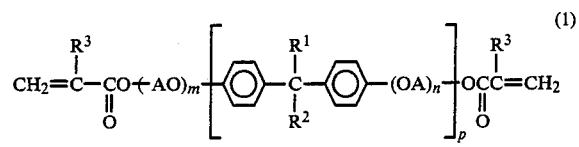

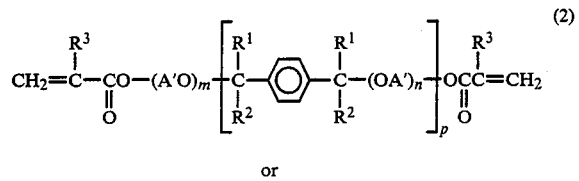

or wherein $R^1$ and $R^2$ are each H, $CH_3$ or $CF_3$, $R^3$ is H, $CH_3$ or F, A is $-CH_2-$, $-CH_2CH_2-$, $-CH_2CH(CH_3)-$, $-CH(OH)-$, $-CH_2CH(OH)CH_2-$, $-CH(OCOCH_3)-$ or $-CH_2CH(OCOCH_3(CH_2-$, A' is the same group as A or $-CH_2CH_2CH_2-$, 2 is an alkylene group having 2 to 10 carbon atoms, m and n are each zero or a number of 1 to 5, p is a number of 1 to 3, q is a number of 1 to 5, provided that at least one of $R^1$ and $R^2$ is $CF_3$ when $R^3$ is H or $CH_3$.

17 Claims, No Drawings

DENTAL MATERIAL

FIELD OF THE INVENTION

The present invention relates to a dental material comprising a copolymer which comprises a fluorine-containing acrylic ester monomer.

BACKGROUND OF THE INVENTION

Recently, with developments in polymer chemistries and industries, various dental materials which are prepared from a high molecular weight material have been investigated.

Although attention has been paid to functional materials, for example, to a photopolymerized type restoration material, a crown material or an adhesive high molecular weight material, these functional materials are quite novel as dental materials and are considered as having promoted technical innovation in the dental medical system.

As examples of the functional materials of these dental materials used, are polymers of the following compounds.

3G: Triethylene glycol dimethacrylate $$CH_2=C(CH_3)COO(CH_2CH_2O)\text{-}_3\text{---}COC(CH_3)=CH_2,$$

Bis-GMA: 2,2-Bis[4-(3-methacryloxy-2-hydroxypropoxy)phenyl]propane

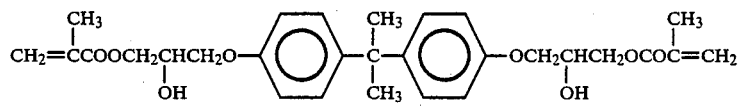

and Bis-MEPP: 2,2-Bis(4-methacryloxyethoxyphenyl)-propane

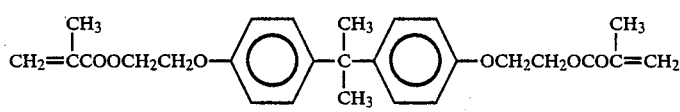

SUMMARY OF THE INVENTION

An object of the present invention is to provide a novel dental material comprising a copolymer which exhibits superior characteristics to those containing polymers of the above compounds.

The above and other objects of the present invention will become apparent from the following description.

The present invention provides a dental material comprising a high molecular weight copolymer which comprises at least 10% by weight of a polymeric unit of at least one of the following monomers

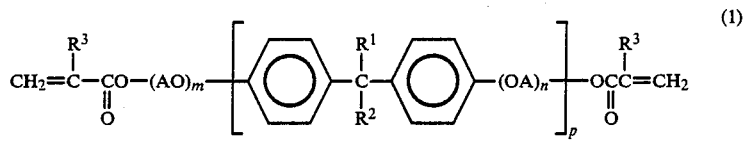 (1)

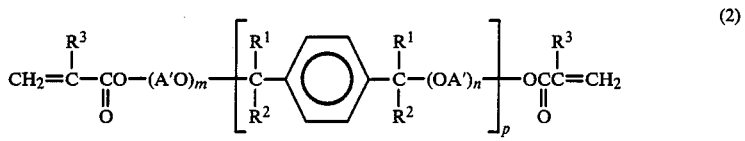 (2)

 (3)

wherein $R^1$ and $R^2$ are each H, $CH_3$ or $CF_3$, $R^3$ is H, $CH_3$ or F, A is $-CH_2-$, $-CH_2CH_2-$, $-CH_2CH(CH_3)-$, $-CH(OH)-$, $-CH_2CH(OH)CH_2-$, $-CH(OCOCH_3)-$ or $-CH_2CH(OCOCH_3)CH_2-$, A' is the same group as A or $-CH_2CH_2CH_2-$, Z is an alkylene group having 2 to 10 carbon atoms, m and n are each zero or a number of 1 to 5, p is a number of 1 to 3, q is a number of 1 to 5, provided that at least one of $R^1$ and $R^2$ is $CF_3$ when $R^3$ is H or $CH_3$.

In the above, A represents $-CH_2-$, $-CH_2CH_2-$, $-CH_2CH(CH_3)-$, $-CH(OH)-$, $-CH_2CH(OH)CH_2-$, $-CH(OCOCH_3)-$ or $-CH_2CH(OCOCH_3)CH_2-$, A' represents the same group as A or $-CH_2CH_2CH_2-$, and Z is an alkylene group having 2 to 10 carbon atoms which may branch.

The dental material of the present invention has various uses, for example, it could be used in crown restoration materials, adhesive materials, artificial crown materials and denture base materials.

The copolymer of the present invention can be prepared by copolymerising at least 10% by weight of at least one monomer of the above formulae (1) to (3), and up to 90% by weight of a comonomer.

The preferred examples of the comonomer are acrylic acid, methacrylic acid and esters thereof. The esters are preferably alkyl ($C_{1\sim20}$) esters, and polyethylene glycol esters, a trimethylolpropane ester and the like. Also preferred are polyalcohol esters, such as polyethylene glycol diacrylate and trimethylolpropane triacrylate.

It is possible to use other comonomers in an amount which does not deteriorate the characteristics of the present dental material.

The present copolymer can be prepared by polymerizing the above monomers and comonomers by a conventional method used in the polymerization of an ethylenically unsaturated monomer. For example, the present copolymer can be and is even preferably obtained by a bulk polymerization method. Molding is easily conducted in such a method. The present invention can also be obtained by powder-liquid polymerization method which is often used in dentistry. Further, the copolymer can be prepared by photopolymerization by irradiation with ultraviolet ray or visible ray, or by suspension polymerization. It is preferable to use a polymerization initiator in polymerization method which employs a heating step.

The polymerization initiator which is usually used is a compound which decomposes at approximately room temperature and produces a radical. The polymerization initiator includes tri-n-butylborane and like alkylated metals which react with oxygen to produce a radical, peroxides (benzoyl peroxide, acetyl peroxide, lauroyl peroxide, cumene hydroperoxide, methyl ethyl ketone peroxide, t-butyl peroxybenzoate, etc.) and a combination of the above peroxide and an accelerator (tertiary amine, cobalt salt of naphthenic acid or octenoic acid, transition metal ion, p-toluenesulfonic acid, amine salt of sulfinic acid, etc.). Each of the above polymerization initiator and accelerator is used preferably in an amount of about 0.1 to 2.5 parts by weight per 100 parts by weight of the monomer.

A photosensitizer is usually used in the polymerization of a monomer with irradiation of ultraviolet ray or visible ray. As the photosensitizer, benzophenone, nitrofluorene, 5-nitroacenaphthene or the like is used when the irradiation is conducted with ultraviolet ray, camphorquinone or the like is used when visible ray is the irradiation source.

It is possible to add an additive to the present dental material which is used in a plastic dental material, such as silica, alumina and silicon nitride.

The present dental material has an equivalent or superior mechanical strength to those prepared by the use of the conventional Bis-DMA, 3G or Bis-GMA materials, and is also excellent particularly in dimensional stability and non-water absorbency, hence excellent in durability.

In the present invention, at least one of the monomers of formulae (1) to (3) is used in the form of a polymer. Alternatively, at least one of these monomers could be added to a dental composition and then polymerized to prepare a dental material of the present invention.

The present invention will be explained by the following examples. In the following, all parts are by weight.

EXAMPLE 1

Into a glass tube were placed 29 parts of 1,1,1,3,3,3-hexafluoro-2,2-bis(4-methacryloxyphenyl)propane (Bis F-DMA) of the formula

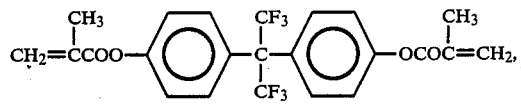

71 parts of methyl methacrylate (MMA) and 0.5 part of benzoyl peroxide. The glass tube was sealed and the content was bulk polymerized at 55° C. for 24 hours and further at 100° C. for 15 hours to obtain Copolymer A.

EXAMPLE 2

A polymerization was conducted in the same manner as in Example 1 except that 2,2-bis[4-(α-fluoroacryloxy)phenyl]propane (Bis-DFA) of the formula

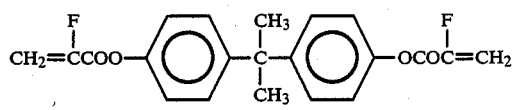

was used in place of Bis F-DMA to obtain Copolymer B.

EXAMPLE 3

A polymerization was conducted in the same manner as in Example 1 except that 1,1,1,3,3,3-hexafluoro-2,2-bis[4-(α-fluoroacryloxy)phenyl]propane (Bis F-DFA) of the formula

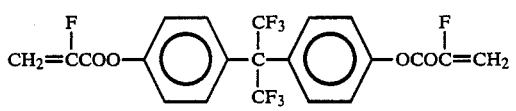

was used in place of Bis F-DMA to obtain Copolymer C.

EXAMPLE 4

A polymerization was conducted in the same manner as in Example 1 except that 38 parts of 1,4-bis(1,1,1,3,3,3-hexafluoro-2-methacryloxypropyl)benzene (FB-DMA) of the formula

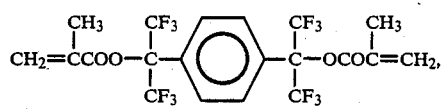

MMA (62 parts) and 0.5 part of benzoyl peroxide were used to prepare Copolymer D.

EXAMPLE 5

A polymerization was conducted in the same manner as in Example 4 except that 1,4-bis(1,1,1,3,3,3-hexafluoro-2-fluoroacryloxypropyl)benzene [a mixture of meta compound and para compound (molar ratio=4/1), FB-DFA] was used in place of FB-DMA to obtain Copolymer E.

EXAMPLE 6

A polymerization was conducted in the same manner as in Example 1 except that 41 parts of 1,1,1,3,3,3-hexafluoro-2,2-bis[4-(3-methacryloxy-2-hydroxypropoxy)phenyl]propane (Bis F-GMA) of the formula

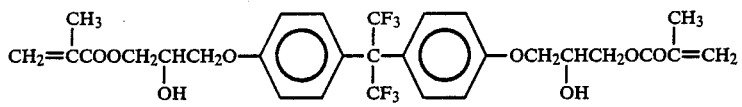

were used to obtain copolymer F.

EXAMPLE 7

A polymerization was conducted in the same manner as in Example 1 except that 44 parts of

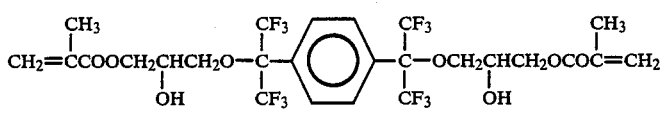

(FB-GMA), MMA (56 parts) and 0.5 part of benzoyl peroxide were used to obtain Copolymer G.

COMPARISON EXAMPLE 1

A polymerization was conducted in the same manner as in Example 1 except that 2,2-bis(4-methacryloxyphenyl)propane (Bis-DMA) of the formula

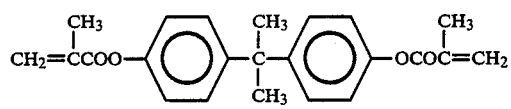

was used in place of Bis F-DMA to prepare Copolymer H.

COMPARISON EXAMPLE 2

A polymerization was conducted in the same manner as in Example 1 except that 24 parts of triethylene glycol dimethacrylate (3G), MMA (76 parts) and 0.5 part of benzoyl peroxide were used to prepare Copolymer I.

COMPARISON EXAMPLE 3

A polymerization was conducted in the same manner as in Example 1 except that 36 parts of 2,2-bis[4-(3-methacryloxy-2-hydroxypropoxy)phenyl]propane (Bis-GMA), MMA (64 parts) and 0.5 part of benzoyl peroxide were used to obtain Copolymer J.

TEST EXAMPLE 1

The copolymers of Examples and Comparison Examples were checked for mechanical properties. The results are given in Table 1.

Test method (1) Compressive strength test

A copolymer of 4 mm in diameter and of 8 mm in height was used as a sample. The copolymer was immersed in water at 37° C. for 24 hours and tested by No. 9 method of American Dental Association (ADA) at a crosshead speed of 2.5 mm/min. with the use of an autograph IS-500 of Shimadzu Seisakusho.

(2) Indirect tensile strength test

A copolymer of 6 mm in diameter and of 5 mm in height was used as a sample. The copolymer was immersed in water at 37° C. for 24 hours and tested by Diametral method at the same crosshead speed as above. In the Table, (a) shows the proportional breaking and (b) shows the breaking point.

(3) Bending strength and bending elasticity test

A copolymer of 4 mm in diameter and of 25 mm in height was used as a sample. The copolymer was immersed in water at 37° C. for 50 hours. Three of these samples were tested by bending test method (distance between supports: 20 mm) at a crosshead speed of 1 mm/min.

(4) Abrasion test with a toothbrush

A copolymer of $10\phi \times 2$ mm was used as a sample. The sample was checked for weight loss by the use of an abrasion test machine K172 of Tokyo Giken Co., Ltd., at 5 cm of one stroke, load of 132 g/sample and 30000 strokes. Abrasion volume was calculated from the weight loss and specific gravity of the sample.

TEST EXAMPLE 2

Water absorption amount (mg/cm$^2$) was measured with the use of copolymer samples ($10\phi \times 1$ mm) of Examples 1 to 5 and Comparison Example 1, after having been immersed in water at 37° C. for 7 days according to ADA standard. The results are shown in Table 2.

TABLE 1

| | copolymer | compressive strength (kgf/cm$^2$) | indirect tensile strength (kgf/cm$^2$) | bending strength (kgf/cm$^2$) | bending elasticity $\times 10^2$kgf/cm$^2$) | abrasion volume (mm$^3$) |
|---|---|---|---|---|---|---|
| Ex. 1 | A | 1550 | 550(a) | 3500 | 530 | 6.0 |
| Ex. 2 | B | 1680 | 610(a) | 3750 | 760 | 4.9 |
| Ex. 3 | C | 1680 | 540(a) | 3250 | 530 | 5.1 |
| Ex. 4 | D | 1280 | 550(b) | 3500 | 520 | 10.3 |
| Ex. 5 | E | 1330 | 520(b) | 3500 | 535 | 8.7 |
| Ex. 6 | F | 1380 | 450(b) | 3200 | 550 | 8.4 |
| Ex. 7 | G | 1340 | 470(b) | 3100 | 580 | 10.4 |
| Com. Ex. 1 | H | 1550 | 500(a) | 3500 | 550 | 5.8 |
| Com. Ex. 2 | I | 1200 | 525(b) | 3250 | 430 | 6.8 |
| Com. Ex. 3 | J | 1340 | 510(b) | 3600 | 535 | 7.9 |

TABLE 2

| | water absorption amount (mg/cm²) | | water absorption amount (mg/cm²) |
| --- | --- | --- | --- |
| Ex. 1 | 0.80 | Ex. 4 | 0.74 |
| 2 | 0.76 | 5 | 0.57 |
| 3 | 0.70 | Com. Ex. 1 | 1.00 |

TEST EXAMPLE 3

Water absorption amount was measured with respect to the copolymers of Examples 6 and 7 and Comparison Examples 2 and 3 in the same manner as in Test Example 2. The results are shown in Table 3.

TABLE 3

| | water absorption amount (mg/cm²) | | water absorption amount (mg/cm²) |
| --- | --- | --- | --- |
| Ex. 6 | 0.99 | Com. Ex. 2 | 1.38 |
| 7 | 1.07 | 3 | 1.60 |

EXAMPLE 8

Into a cylindrical vessel, 4 mm in diameter and 6 mm in depth, were placed a mixture of 2 ml of a composition and 3 g of filler, the composition being composed of Bis-DFA(2 g), 3GF(5 g), CQ(0.07 g) and DEA-EM(0.156 g), and the filler being Aerosil OX50 treated with 3-MPS (5 wt%). The vessel was capped with a celluloid plate and the content was irradiated with a light having a wavelength of 494 nm for 60 seconds to obtain a photocured product having a depth of 5.4 mm.

In the above,

3GF: Triethylene glycol di(α-fluoromethacrylate)
CQ: Camphorquinone
DEAEM: 2-Diethylaminoethyl methacrylate

COMPARISON EXAMPLE 4

A photocured product having a depth of 2.1 mm was obtained in the same manner as in Example 8, except that Bis-DMA and 3G were used respectively in place of Bis-DFA and 3GF.

It is apparent from the above the cured product of Example 8 has about 2.6 times dimensional stability (small in shrinkage) than that of Comparison Example 4.

EXAMPLE 9

On a glass plate of 6×6×3 mm was placed about 0.01 g of a mixture of Example 8. The mixture was irradiated from 2 mm-distance with a light having a wavelength of 494 nm for 30 seconds to obtain a photocured product. The product had surface hardness (Vickers hardness, Hv) of 13.5.

COMPARISON EXAMPLE 5

A photocured product having surface hardness (Hv) of 2.0 was obtained in the same manner as in Example 9, except that a mixture of Comparison Example 4 was used.

It is apparent from the above that the cured product of Example 9 has a surface hardness of about 6.8 times surface hardness than that of Comparison Example 5.

We claim:

1. A dental material comprising a copolymer which comprises at least 10% by weight of polymeric units of the following monomers:

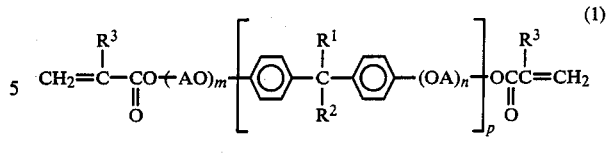

and

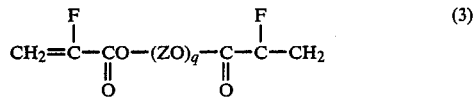

wherein $R^1$ and $R^2$ are each H, $CH_3$ or $CF_3$, $R^3$ is H, $CH_3$ or F, A is $-CH_2-$, $-CH_2CH_2-$, $-CH_2CH(CH_3)-$, $-CH(OH)-$, $-CH_2CH(OH)CH_2-$, $-CH(OCOCH_3)-$ or $-CH_2CH(OCOCH_3)CH_2-$, Z is an alkylene group having 2 to 10 carbon atoms, m and n are each zero or a number of 1 to 5, p is a number of 1 to 3, q is a number of 1 to 5, provided that at least one of $R^1$ and $R^2$ is $CF_3$ when $R^3$ is H or $CH_3$.

2. The dental material of claim 1, wherein the copolymer further comprises up to 90% by weight of polymeric units of a comonomer.

3. The dental material of claim 1, wherein the copolymer further comprises polymeric units of diethylaminoethyl methacrylate.

4. The dental material of claim 2, wherein the comonomer is acrylic acid, methacrylic acid or an ester thereof.

5. The dental material of claim 2, wherein the comonomer is methyl methacrylate.

6. The dental material of claim 1, wherein at least one $R^3$ of monomer (1) is F.

7. The dental material of claim 1, wherein A of monomer (1) is $-CH_2-$, $-CH(OH)-$, $-CH_2CH(OH)CH_2-$, $-CH(OCOCH_3)-$ or $-CH_2CH(OCOCH_3)CH_2-$.

8. The dental material of claim 1, wherein monomer (1) is 1,1,1,3,3,3-hexafluoro-2,2-bis(4-methacryloxyphenyl)propane.

9. The dental mateial of claim 1, wherein monomer (1) is 1,1,1,3,3,3-hexafluoro-2,2-bis[4-(α-fluoroacryloxy)phenyl]propane.

10. The dental material of claim 1, wherein monomer (1) is 1,1,1,3,3,3-hexafluoro-2,2-bis[4-(α-fluoroacryloxy)phenyl]-propane.

11. The dental material of claim 1, wherein monomer (1) is 1,1,1,3,3,3-hexafluoro-2,2-bis[4-(3-methacryloxy-2-hydroxypropoxy)-phenyl]propane.

12. The dental material of claim 8, wherein the copolymer further comprises polymeric units of methyl methacrylate.

13. The dental material of claim 9, wherein the copolymer further comprises polymeric units of methyl methacrylate.

14. The dental material of claim 10, wherein the copolymer further comprises polymeric units of methyl methacrylate.

15. The dental material of claim 11, wherein the copolymer further comprises polymeric units of methyl methacrylate.

16. The dental material of claim 9, which further comprises a filler.

17. The dental material of claim 9, wherein monomer (3) is triethylene glycol di(α-fluoromethacrylate).

* * * * *